United States Patent
Aho et al.

(10) Patent No.: US 6,884,518 B2
(45) Date of Patent: Apr. 26, 2005

(54) MATERIAL SUITABLE FOR AN INDIVIDUAL'S TISSUE RECONSTRUCTION

(76) Inventors: Allan Aho, Yliopistonkatu 1 A 9, FIN-20100 Turku (FI); Antti Yli-Urpo, Värttinäkatu 17, FIN-20660 Littoinen (FI); Pertti Viitaniemi, Pohjantähdentie 2 Q 56, FIN-00740 Helsinki (FI)

( * ) Notice: Subject to any disclaimer, the term of this patent is extended or adjusted under 35 U.S.C. 154(b) by 147 days.

(21) Appl. No.: 10/220,016

(22) PCT Filed: Feb. 21, 2001

(86) PCT No.: PCT/FI01/00171

§ 371 (c)(1),
(2), (4) Date: Nov. 25, 2002

(87) PCT Pub. No.: WO01/62109

PCT Pub. Date: Aug. 30, 2001

(65) Prior Publication Data

US 2003/0143255 A1 Jul. 31, 2003

(30) Foreign Application Priority Data

Feb. 25, 2000 (FI) .............................................. 20000439

(51) Int. Cl.[7] .............................................. B32B 21/04
(52) U.S. Cl. .......................... 428/537.1; 623/11; 623/12; 623/16; 623/18; 623/20; 623/22; 623/23; 623/66.1; 424/422; 424/428; 424/484; 424/423; 424/501
(58) Field of Search .................. 428/537.1; 424/422, 424/423, 428, 484, 501, 426; 623/66.1, 11, 12, 16, 18, 20, 22, 23

(56) References Cited

U.S. PATENT DOCUMENTS

| 4,257,405 | A | | 3/1981 | Colville ..................... 128/1 R |
|---|---|---|---|---|
| 5,123,923 | A | * | 6/1992 | Pommier et al. ......... 623/23.58 |
| 5,152,793 | A | * | 10/1992 | Pommier et al. ......... 623/23.58 |
| 6,353,038 | B1 | * | 3/2002 | Aho et al. .................. 523/105 |
| 6,451,059 | B1 | * | 9/2002 | Janas et al. .............. 623/23.51 |
| 6,573,340 | B1 | * | 6/2003 | Khemani et al. ........... 525/437 |
| 6,630,153 | B1 | * | 10/2003 | Long et al. ................. 424/422 |

OTHER PUBLICATIONS

Colville et al., "Wood Anatomy and the Use of Carbonised Wood as a Matrix for Bone Regeneration in Animals," 1 *IAWA Bull.* 3 (1979) and Biosis:PREV197968052003.

WPI/Derwent, "Mfg. Calcium Phosphate Coating Layer Used in Mfg. Artificial Organ—By Applying Calcium Phosphate Precursor Layer Onto Core By Electrodeposition, Then Heat Treating".

* cited by examiner

Primary Examiner—Leszek Killiman
(74) Attorney, Agent, or Firm—James C. Lydon

(57) ABSTRACT

A material suitable for the reconstruction of an individual's tissue, particularly supportive tissue such as bone tissue, insertable into the tissue. The material is characterized by being composed of wood heat-treated within the temperature range of 100–220° C. in the presence of water vapor. The invention also relates the use of the wood.

22 Claims, 1 Drawing Sheet

Half joint

Half joint

Hemijoint

Long bone segment

Hip prosthesis

MATERIAL SUITABLE FOR AN INDIVIDUAL'S TISSUE RECONSTRUCTION

The application is a U.S. Nation Stage of International application PCT/FI01/00171, filed Feb. 21, 2001 and published on Aug. 30, 2001 in the English Language.

The invention relates to the material defined in the preamble of Claim 1 and to the use thereof.

BACKGROUND

The publications referred to below and used for elucidating the background of the invention and the state of the art are to be viewed as being incorporated into the description of the invention presented below.

By "tissue" is meant herein both hard tissue (bone, tooth and cartilage) and soft tissue. A supportive tissue may be a hard tissue or soft tissue structure, such as a tendon, connective tissue or ligament.

Materials tested and used for the reconstruction of supportive tissue, in particular bone tissue, include calcium phosphate based materials made, for example, from bovine bone, hydroxyapatite prepared by chemical methods, calcium phosphate, tri-calcium phosphate, coral-based hydroxyapatites, bioactive glasses, metals or metal alloys (e.g. titanium or vitallium), a large group of polymers, and bone tissue itself, either the patient's own bone (autograft) or bank bone (allograft) (Aho & Heikkilä 1997). There are adverse effects associated with all of these materials because of the complicated manufacturing process of the material, unsatisfactory strength of the material, its cumbersome handling property or its unsatisfactory workability, or potential risk of contagious disease. There has been a search for a material which would not have the above-mentioned adverse effects and which would additionally correspond to bone tissue by its structure and resilience and be easily workable. By workability is meant in particular the shaping of a piece, sawing, carving and drilling of the material, and the attaching of the piece at its targeted site. The workability of the known materials mentioned above is unsatisfactory. Furthermore, they are brittle and prone to break.

In 1997 there was published in the literature, in the form of an abstract, a report on experimentation with wood, i.e. juniper, in rabbit bone (Gross et al., 1997). The juniper wood used in this experimentation was, however, in no manner pre-treated.

OBJECT OF THE INVENTION AND SUMMARY OF THE INVENTION

The object of the present invention is to provide a novel material suitable for the reconstruction of an individual's tissue, in particular the reconstruction of supportive tissue, such as bone tissue.

A particular object is to provide a material that allows the formation of new tissue inside the material and/or favors the integration of tissue with the surface of the said material.

It is also an object to provide a material that can be combined with a bioactive material, various active agents or agents promoting biodegradability.

It is also an object to provide a material from which a piece with good strength properties can be made, the workability of which is good, and the structure of which, nevertheless, allows the formation of new tissue inside the piece and/or integration of tissue with it.

These objects are achieved with the material according to the invention, the characteristics of the material being given in the claims.

The object of the invention is thus a material suitable for an individual's tissue reconstruction, in particular the reconstruction of supportive tissue, such as bone tissue, insertable into the tissue, the material being characterized in that it is made up of wood heat-treated within the temperature range of 100–220° C. in the presence of water vapor.

The invention also relates to the application of the novel material to various medical or dental, in particular surgical or therapeutic purposes, i.e. for rectifying various defects of supportive tissue, in particular bone or the skeletal structure; as part of a bone; as articular cartilage surfaces; as filler for bone cavities; for the reconstruction of long bones; as correction plates for the fundus of the eye or facial bones or as a filler material for cavities; as a cranial plate; as a nail; as a screw; as a piece for vertebral repair; as a bone cement component; as a joint prosthesis or an implant either as such or combined with metal prostheses, metal plates or metal implants; as a jaw and/or tooth implant; as a mineralizing toothpick; as an occlusal splint; as a parodontal filler; as tooth cement; as surgical paste; as a tissue-guiding membrane or tube; as a protective fabric; as a wound dressing fabric; in combined use with autogenic or allogenic bone; or as an ingredient in other biomaterial preparations, such as plastics (e.g. acrylics) or various compositions.

BRIEF DESCRIPTION OF THE DRAWINGS

The present invention will be understood and appreciated more fully from the following detailed description taken in conjunction with the attached drawings in which.

PREFERRED EMBODIMENTS AND A DETAILED DESCRIPTION

Figure 1:
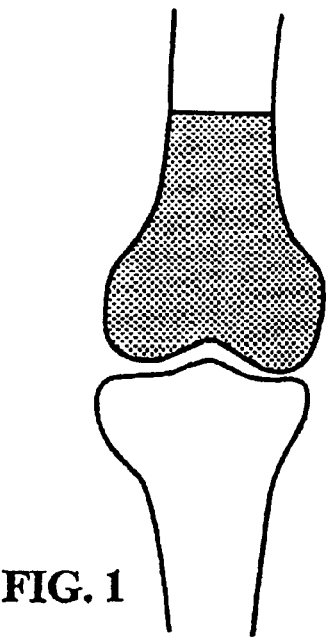
FIG. 1 illustrates a half joint according to the invention.

The wood used in the present invention may be either hardwood or softwood. Usable hardwood species are primarily birch, aspen, oak, alder and poplar, and usable softwood species pine, juniper, spruce and larch.

Rendering wood usable in a tissue presupposes its sterilization, i.e. the elimination of any bacteria, molds, fungi and spores present in it. This is achieved by heat-treating the wood material within the temperature range of 100–220° C. in the presence of water vapor, whereby the igniting of the wood is prevented. Heating to a temperature above 100° C. changes the physical and chemical properties of wood. Within the temperature range of 100–200° C., water leaves the wood, and the polymer chains of carbohydrates break and free acids are formed. The carbohydrates break down further and the pyrolysis of lignin and wood begins (Pecina & Paprycki 1988). What is essential is thus the partial breaking down in various ways of the principal components of wood, i.e. cellulose, hemicellulose and lignin.

The acetic acid formed in the breaking down of cellulose and hemicellulose de-polymerizes the microfibrils of cellulose. Soluble sugars are formed in the hydrolysis of hemicellulose (Hillis 1984). During heat treatment, polysaccharides are also formed by hot and cold extraction (Fengell 1966). The pentosans of hardwood break down more readily than the hexanes of softwood (Kollman & Fengell 1965), and the effect of the heat treatment on the wood of different species depends on the type and amount of the hemicellulose. Lignin withstands heat best.

The wood material according to the present invention is heat treated with humid air in the presence of water vapor (Viitaniemi & Jämsä 1996). This method is also described in Finnish patent FI 103834. Such a method has also been used in the wood industry for improving the decay resistance of wood. Owing to the heat treatment the color of the wood darkens, its decay resistance and mold resistance increase strongly, its moisture expansion decreases by 80–90%, and its bending strength decreases by 10–15%. Changes are observable in the fiber structure of the wood, e.g. longitudinal cracks in the cell walls.

According to a suitable embodiment, care is taken during the heat treatment that the difference between the internal temperature of the piece of wood and the temperature of the medium (air and water vapor) surrounding the piece of wood is limited, preferably it is at maximum approx. 30° C. In this manner it is ensured that cracks weakening the strength are not formed in the wood material.

The water vapor used is preferably a saturated water vapor.

The wood material thus treated can be worked to the desired shape, allowing also the drilling of holes.

According to another option it is possible first to work pieces of the desired shape from the wood and to heat-treat the pieces only thereafter.

According to a further option, a piece of the desired shape can be prepared by compressing heat-treated wood particles, such as sawdust or wood powder, or particles elongated in the longitudinal orientation of the wood fibers. In the compression it is possible to use suitable additives that promote the coherence of the piece, such as acrylic plastics or other tissue adhesives. A piece compressed from wood particles is suitable for use for purposes wherein strengths are less critical properties. From the elongated wood particles mentioned above it is possible to compress pieces having a desired resilience, tensile strength and plasticity. By varying the size and shape of the particles it is possible to regulate the said properties to a large extent.

According to a further option, wood particles can be used as such (i.e. without compressing them into a piece), for example, as a filler material for bone cavities.

The heat treatment of the wood can be carried out while the wood is either in the form of a relatively large piece or in particulate form.

According to a highly recommended embodiment, a bioactive component is also added to the material according to the invention. By the addition of a bioactive component the integration of the wood structure and the surrounding tissue (bone and/or connective tissue) can be improved and accelerated. The bioactive component may additionally have one or more of the following properties: bonding with tissues or tissue-mineralizing, biocompatible, biodegradable or releasing active agents (e.g. anti-microbial). The bioactive component may be a bioactive glass, a bioactive polymer, a silica gel, e.g. xerogel, Ti gel, a ceramic material, a glass ceramic material, calcium phosphate, hydroxyapatite, coral, or allogenic or autogenic bone, or any mixture of the above-mentioned components (Aho 1993; Heikkilä et al. 1995; Buchholz et al. 1987; LeGeros & LeGeros 1993; Kangasniemi 1993).

The bioactive component may be present in various forms, such as ions, particles, granules, spherules, fibers, rods or films. Thus the bioactive component may be combined with the wood material in different ways.

The combining of the bioactive component with the wood material can be carried out in different ways. If the wood material is in a particulate form, it can be mixed with a particulate bioactive material. When so desired, the mixture can be compressed into a piece. If the wood material is present in the form of a continuous piece of wood, a bioactive material in a finely-divided form may be introduced inside the piece by means of either a gas or a liquid stream. It is thus possible to use pressurized precipitation (whereby a fine powder is transported to the inside of a piece of wood), various mineralization techniques (impregnation with solutions), etc. The bioactive component and the carrier liquid stream may, for example, be present as a solution, in the form of a colloidal solution such as a sol, suspension or emulsion. The bioactive component may also be present as a separate layer relative to a piece shaped from a wood material, for example as a coating or a laminate. A combination of all of the above is also possible.

It is also possible to add to the wood material other substances having physiologically advantageous effects, either as such or together with a bioactive component described above. Such active agents include growth factors, proteins (e.g. bone morphogenetic protein, BMP), drugs (e.g. antibiotics or cytostatic drugs), sugars, hormones (such as hormones having anabolic action), enzymes, other organic substances, such as collagen, hyaluronic acid and antioxidants. Furthermore, it is possible to treat the wood material by using genetic engineering, e.g. by transferring into it a growth-increasing gene (e.g. a virus gene). The type of the additive used is determined by the targeted use on medical grounds, the purpose being to improve and to speed up tissue growth and to affect the basic disease, such as cancerous tissue and/or inflammation.

It is also possible to combine with the wood material a plastics component as a paste, in a soluble form or in a thermoplastic form (e.g. lactide/caprolactone), with which the splintery structure of wood is impregnated by the methods described above.

If it is desired to promote and accelerate the biodegradability of the wood material, also such agents can be added to it. By a special chemical technique this wood material can be treated so that it is caused to degrade in a controlled manner, in which case it may be entirely replaced with the parent tissue, e.g. bone. Further examples of substances of this type are enzymes, such as collagenases and proteases, catepsin, and streptokinase or streptodomase, or gene transfer methods.

The wood material may form a dense or in different degrees porous piece, e.g. a prosthesis. It may be shaped, according to its targeted use, as a rod, plate, membrane or sphere, or to correspond to the required anatomic structure.

It is also possible to manufacture coatings and membranes from the wood material. The wood material may be netlike, filamentous, or in particle form, such as a fiber, powder or granular sawdust, or a shaped piece, such as a plate, tube, rod, nail or screw. The purpose is to use it for the correction of an anatomic structure, but also for attaching it or a bone by means of a wooden nail or other such spike via a bore. The structure according to the invention may also in its piece-like form contain holes or conduits corresponding to the osteonic structure of the shell layer of the bone, and its macrostructure may be tubular, i.e. hollow, corresponding to, for example, the core and overall structure of a long bone. It may be a lamellar plate structure, smooth or modified. The product may be soft, resilient, brittle or hard mineralized.

A material to be fitted in connection with body tissue must, of course, be sterile. In consequence of the heat treatment the microbes present in the wood die, but nevertheless a final sterilization of the product, for example by means of heat or irradiation, is recommended.

Uses of the material according to the invention that can be mentioned include, in supportive tissue structures, bone and cartilage defects. Practical targeted uses include filler material for bone cavities, reconstruction of long bones or flat bones with a plate fastener, core nail or screw, correction plate for the fundus of the eye/facial bones, cranial plate, vertebral repair plate, bone cement component, joint prosthesis, or implant coating for metal prostheses or plates. Applications in the teeth and the jaws include dental implant coating, jawbone implant, occlusal splint, paradontal filler, mineralizing toothpick, paste or dental segment, or surgical paste. Other applications include tissue guiding membrane or tube, cell tissue growing net, frame, protective fabric, wound dressing fabric, joint use with autogenic or allogenic bone, and carrier substance for active agents such as drugs.

Figure 2:
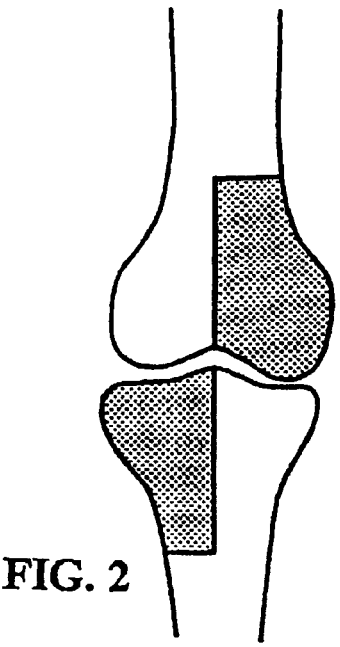
FIG. 2 illustrates a hemijoint according to the invention.
Figure 3:
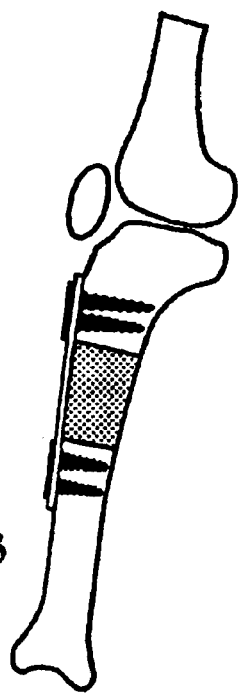
FIG. 3 illustrates a long bone segment according to the invention.
Figure 4:
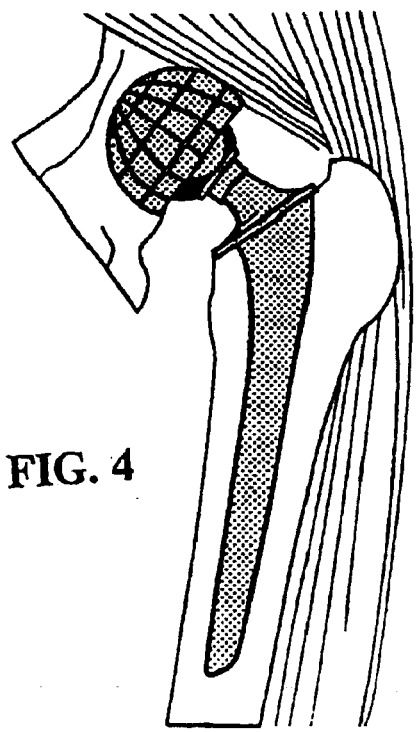
FIG. 4 illustrates a hip prosthesis according to the invention.

The purpose is to use the material according to the invention specifically in the following conditions:
1) Defects arising in connection with bone tumors or re-surgery of hip or knee prostheses; these are defects which are either cavity-like or comprise the cartilage-bone part of the bone epiphysis and the joint, or a segment of the diaphysis or the longitudinal hemisphere of a long bone (cf. FIGS. 1, 2 and 3).
2) Bone defects arising in connection with various fractures in a long bone, flat bones or vertebrae, which would require a bone transplant as a treatment.
3) An joint (hip, knee) prosthesis of a novel type may be made from the material according to the invention (cf. FIG. 4).
4) Developmental and late impairment of the bones and other supportive tissues, also comprising conditions within the scope of dentistry in the jawbones and joints and in teeth, such as congenital developmental anomalies and defects and bone deficiencies developing later in life, for example, those caused by infections, osteoporosis and osteopenia.
5) In dentistry the attachment of implants and dentures, growing and shaping of the bone ridge, toothpicks (mineralizing).
6) A combination of wood cells and bone cells may replace the use of autograft or allograft, i.e. bank bone.

Bone defects arising from cancer surgery can be mentioned as a very concrete targeted use. A malignant or aggressive bone tumor in a long bone may have to be treated by removing a portion of the said long bone surgically, whereby an extensive, for example 10–15 cm long, area where bone is absent is formed. This absent bone can be replaced with a wood piece of the corresponding shape and size (possibly also containing other components, such as a bioactive component and an active agent), which is inserted into the area (e.g. hip bone or leg bone). The piece is attached either with a surgical plate with screws or best with a core nail. In this case the function of the bone and the joint is retained and it is possible for bone tissue to integrate with the said implant (cf. FIGS. 1–4).

The behavior of the material according to the invention in bone is described in greater detail with the help of the following example.

EXAMPLE

In the studies conducted, conical or cylindrical (2.5×5 mm) implants made from heat-treated wood (aspen, birch, pine) were inserted into bores in the cancellous bone of a rabbit's knee. A microscopic examination of the implant cavities at 4–8 weeks showed that in several areas the wood fiber structure was in direct tissue contact with the bone. The connective tissue formed on the edges of the cavities was structurally closely integrated with it. In the interface, macrophages were seen, but no round cells or lymphocytes, i.e. no actual immunogenic reaction was detected. The macroscopically small pieces of wood were clean on the surface of the bone and cartilage, without accumulation of fluid. At twenty weeks the bone was more abundantly attached to the material, and small islands of bone and osteoid tissue were seen in its canalicular inner structure.

Heat-treated wood enables living bone to integrate with the wood fiber structure. This phenomenon is promoted by the partial micro- and macroscopic similarity of the structures of wood and compact bone tissue. There is namely observable in wood a system of wood cells located cylindrically one inside the other, the cells being interconnected by passages running in both the longitudinal and the lateral orientations. In compact bone, e.g. in the cortical bone of a long bone, there are also cylindrical, lamellar tubular, sheet-like structures formed by hydroxyapatite-collagen strands and located one inside another. Blood vessels are located in the center of these, connecting them also in the transverse direction. A bioactive component, e.g. bioactive glass, promotes and further accelerates the integration of the bone tissue with the implant structurally and chemically.

The embodiments cited above are only examples of the implementation of the idea of the invention. For a person skilled in the art it is clear that the various embodiments of the invention may vary within the scope of the claims presented below.

LITERATURE REFERENCES

Aho A J, Heikkilä J T. Bone substitutes and related materials in clinical orthopaedics. In: Advances in Tissue Banking, Vol. 1, eds. Phillips G O, Versen R, Strong M, Nather A. World Scientific, Singapore 1997:73–107.

Aho A J, Heikkilä J T, Andesson Ö H, Yli-Urpo A. Morphology of osteogenesis in bioactive glass interface. Ann Chirurg Gynaecol 1993; 82:145–153.

Bucholz R W, Carlton A, Holmes R. Hydroxyapatite and tricalcium phosphate as bone graft substitutes. Orthop Clin North Am 1987; 18:323–334.

Fengell D. Heiss-und Kaltwasserextrakte von thermisch behandeltem Fichtenholz. Holz Roh Werkst 1966; 24:9–14.

Gross, Ezerietis E, Gardovskis J, Skudra M, Vetra J. Juniper woods as an alternative implant material. 13th Conference of Biomaterials. Göteborg, Sweden Sep. 4–7, 1997. P. 36.

Heikkilä J. Bioactive glass as a bone substitute in experimental and clinical bone defects. Thesis. Ann Univ Turkuensis Ser D Tom 240. Turku 1996.

Heikkilä J T, Aho A J, Aho H J, Yli-Urpo A, Happonen R-P. Bone formation in rabbit cancellous bone defects filled with bioactive glass granules. Acta Orthop Scand 1995; 66:463–467.

Hillis W. High temperature and chemical effects on wood stability. Part 1: General considerations. Wood Sci Technol 1984; 18:281–293.

Kangasniemi I M O. Development of Ca, P-ceramic containing bioactive glass composites. Thesis. University of Leiden, The Netherlands 1993.

Kollman F, Fengell D. Änderungen der chemischen Zusammensetzung von Holz durch thermische Behandlung. Holz Roh Werkst 1965; 23:461–468.

LeGeros R Z, LeGeros J P. Dense hydroxyapatite. In: An introduction to bioceramics, eds. Hench L L, Wilson J, World Scientific, Singapore 1993:139–180.

Pecina H, Paprzycki O. Wechselbeziehungen zwishen der Temperaturbehandlung des Holzes und seiner Benetzbarkeit. Holzforsch Holzverwert 1988; 40:5–8.

Roffael E, Schaller K. Einfluss thermischer behandlung auf Cellulose. Holz Roh Werkst 1971; 29:275–278.

Viitaniemi P, Jämsä S. Puun modifiointi lämpökäsittelyllä. VTT Publications 814. Espoo 1996.

What is claimed is:

1. A tissue reconstruction implant, wherein it is made up of wood heat-treated within a temperature range of 100–220° C. in the presence of water vapor, and has a shape adapted for tissue reconstruction.

2. The implant of claim 1, wherein the wood is treated so that the difference between an internal temperature of the wood and a medium surrounding the wood is limited, and that the water vapor is a saturated water vapor.

3. The implant of claim 2 wherein said difference between the internal temperature of the wood and the medium surrounding the wood is limited to a maximum of approximately 30° C.

4. The implant of claim 1, wherein said implant has been shaped from wood, the shaping having been carried out before the heat treatment of the wood or after it.

5. The implant of 1, wherein said shape of said implant is a plate or a rod.

6. The implant of claim 1, wherein said implant has been made into a desired shape by compressing together wood particles, or particles elongated in the longitudinal orientation of the wood fibers.

7. The implant of claim 6, wherein said wood particles are wood sawdust or wood powder.

8. The implant of claim 1, wherein said implant additionally comprises a bioactive component.

9. The implant of claim 8, wherein the bioactive component, which is in a finely-divided form, is introduced into said wood by means of a liquid or gas stream prior to shaping of the wood into said shape adapted for tissue reconstruction.

10. The implant of claim 8, wherein the bioactive component, which is present in a particulate form, is mixed with wood material in a particulate form, whereafter the mixture is compressed into said shape adapted for tissue reconstruction.

11. The implant of claim 8, wherein the bioactive component is present as a layer separate relative to the wood.

12. The implant of claim 4, wherein said layer is a coating or laminate.

13. The implant of claim 1, wherein the bioactive component is a member of the group consisting of bioactive glass, a bioactive polymer, silica gel, Ti gel, a ceramic material, a glass ceramic material, calcium phosphate, hydroxyapatite, coral, allogenic or autogenic bone, or any mixture thereof.

14. The implant of claim 1, further comprising an active agent selected from the group consisting of a drug, a growth factor, a protein, a sugar, a hormone, an enzyme, a collagen, an antioxidant, a substance degrading the material in a controlled manner, and any mixture thereof.

15. The implant of claim 14, wherein said drug is an antibiotic or a cytostatic drug.

16. The implant of claim 1, further comprising a substance promoting the biodegradability of the implant.

17. A method for reconstructing an individual's tissue, comprising surgically exposing at least one location in an individual's body where tissue is to be reconstructed, inserting the implant of claim 1 into said location, and surgically closing said location.

18. The method of claim 17, wherein said tissue to be reconstructed is selected from the group consisting of supportive tissue, the surface of joint cartilage; facial bones, and cranial plates.

19. The method of claim 18, wherein said supportive tissue comprises bone or the skeletal system.

20. The method of claim 17, wherein said implant is in a form selected from the group consisting of a filler material for bone cavities; a filler material of cavities; a nail; a screw; a repair piece of a vertebra; a bone cement component; a joint prosthesis or implant; a jawbone, a tooth; a mineralizing toothpick; an occlusal splint; a parodontal filler material; a tooth cement; a surgical paste; as a tissue-guiding membrane or tube; a protective fabric; and a wound dressing fabric.

21. The method of claim 17, wherein said implant is combined with at least one metal joint prosthesis, plate or implant, or said implant is combined with autogenic bone.

22. The method of claim 17, wherein said implant is combined with at least one other component to form a biomaterial preparation, wherein said component comprises an acrylic.

* * * * *